United States Patent [19]
Inoue et al.

[11] Patent Number: 6,063,066
[45] Date of Patent: May 16, 2000

[54] DISPOSABLE BODY FLUIDS ABSORBENT GARMENT HAVING DISPOSAL SECURING MEANS

[75] Inventors: Yasushi Inoue; Hiroyuki Soga, both of Kagawa-ken, Japan

[73] Assignee: Uni-Charm Corporation, Ehime-ken, Japan

[21] Appl. No.: 09/111,334

[22] Filed: Jul. 7, 1998

[30] Foreign Application Priority Data

Jul. 10, 1997 [JP] Japan ................................ 9-184908

[51] Int. Cl.[7] .................................................. A16F 13/15
[52] U.S. Cl. .................... 604/385.1; 604/389; 428/343
[58] Field of Search ................................ 604/385.1, 389

[56] References Cited

U.S. PATENT DOCUMENTS 5,176,671  1/1993  Roessler et al. ....................... 604/391
5,575,784  11/1996  Ames-Ooten et al. ............... 604/385.1
5,807,371  9/1998  Toyoda et al. ....................... 604/385.1

FOREIGN PATENT DOCUMENTS 0 732 094A  9/1996  European Pat. Off. .
6-77722 U  11/1994  Japan .
99/17693A  4/1999  WIPO .

Primary Examiner—John G. Weiss
Assistant Examiner—Carie Mager
Attorney, Agent, or Firm—Barnes & Thornburg

[57] ABSTRACT

A disposable body fluids absorbent garment is provided with disposal securing means including a tape fastener used to secure the garment in its rolled up state for disposal. The tape fastener comprises an extendible intermediate tape section and a pair of inelastic and adhesive distal end tape sections extending from the intermediate tape section in a direction of its extension. A region of the tape fastener extending between the pair of distal end tape sections is partially bonded to an outer surface of a backsheet of the garment so that this region is not inseparable from the backsheet when the tape fastener is pulled in an extension direction thereof.

7 Claims, 2 Drawing Sheets

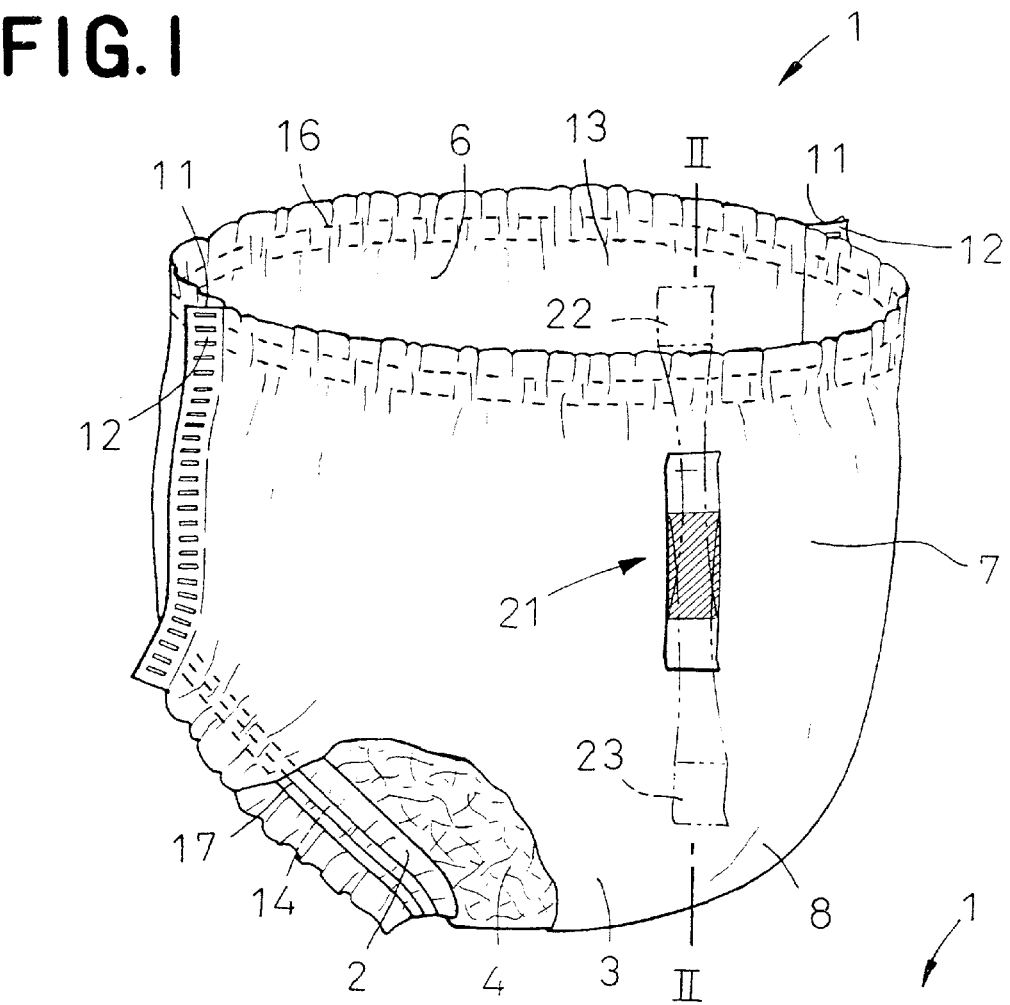
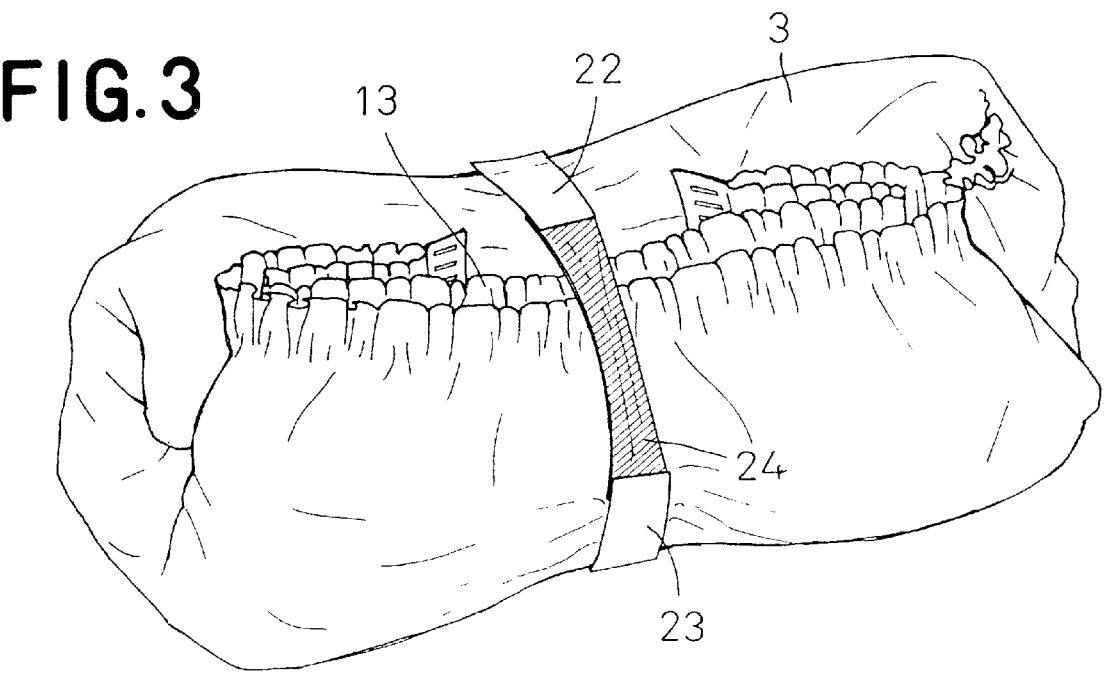

DISPOSABLE BODY FLUIDS ABSORBENT GARMENT HAVING DISPOSAL SECURING MEANS

BACKGROUND OF THE INVENTION

This invention relates to disposable body fluids absorbent garments, such as disposable diapers, training pants, diapers for incontinent patients or sanitary napkins, provided with means used to secure the used garments in their rolled up state for disposal.

Japanese Laid-Open Utility Model application No. Hei6-77722 discloses a pull-on diaper provided with a tape fastener having one end fixed on an outer surface of a backsheet of the diaper and extendible from a crotch region toward a waist-opening of the diaper. The diaper smeared with excretion may be rolled up from the crotch region toward the waist-opening with the tape fastener being laid outside, then the tape fastener is stretched until its one end reaches a farther side of the waist-opening and finally an adhesive zone on an inner surface of the tape fastener is anchored to the backsheet on the farther side of the waist-opening. In this manner, the diaper can be rolled up without exposure of excretion-smeared locations and therefore can be disposed in a desirable condition from the hygienic viewpoint.

However, the above-mentioned diaper of prior art is inconvenient depending on a position at which the tape fastener is fixed to the backsheet. Specifically, when the diaper is rolled in the reverse direction instead of rolling it from the crotch region toward the waist-opening, it may be difficult or impossible to use the tape fastener. This is for the reason that a free end of the tape fastener to be held by a wearer or a helper may be rolled together with the diaper or prevented from being properly handled by the wearer or the helper.

SUMMARY OF THE INVENTION

In view of the problem as has been described above, it is a principal object of the invention to provide a disposable body fluids absorbent garment allowing the garment after use to be properly rolled up regardless of the directions in which the tape fastener is stretched.

The object set forth above is achieved, according to the invention, by a disposable body fluids absorbent garment comprising a laminate structure formed by a liquid-permeable topsheet, a liquid-impermeable backsheet and a liquid-absorbent core disposed between these two sheets; and disposal securing means provided on an outer surface of said backsheet so as to be used to roll up said laminate structure, wherein: said disposal securing means comprises a tape fastener including an extendible intermediate tape section and a pair of inelastic and adhesive distal end tape sections extending from longitudinally opposite ends of said intermediate tape section in a direction in which said intermediate tape section is extendible wherein a region of said tape fastener extending between said pair of distal end tape sections and including said intermediate tape section is partially bonded to said outer surface of said backsheet so that said region is substantially inseparable from said outer surface of said backsheet when said tape fastener is pulled in an extension direction thereof.

According to an embodiment of the invention, said tape fastener is bonded to said outer surface of said backsheet in the proximity of a longitudinally middle sub-section of said intermediate tape section so that said middle sub-section is substantially inseparable from said outer surface of said backsheet against a stretch force exerted on said tape fastener.

According to another embodiment of the invention, said tape fastener is temporarily secured to said outer surface of said backsheet by means of adhesive at respective proximal ends of said distal end tape sections, said proximal ends being contiguous to said intermediate tape section, so that said proximal ends are easily separated from said outer surface of said backsheet when said distal end tape sections are pulled so as to be folded in a direction opposed to a direction in which they normally extend from said intermediate tape section, respectively, but said proximal ends are substantially inseparable from said outer surface of said backsheet when said distal end tape sections are pulled in said direction in which they normally extend from said intermediate tape section.

BRIEF DESCRIPTION OF THE DRAWINGS

FIG. 1 is a perspective view showing a disposable body fluids absorbent garment with disposal securing means according to the invention, in the form of a disposable diaper, as partially broken away;

FIG. 3 is a perspective view showing the diaper as rolled up for disposal; and

DESCRIPTION OF THE PREFERRED EMBODIMENTS

Figure 2:
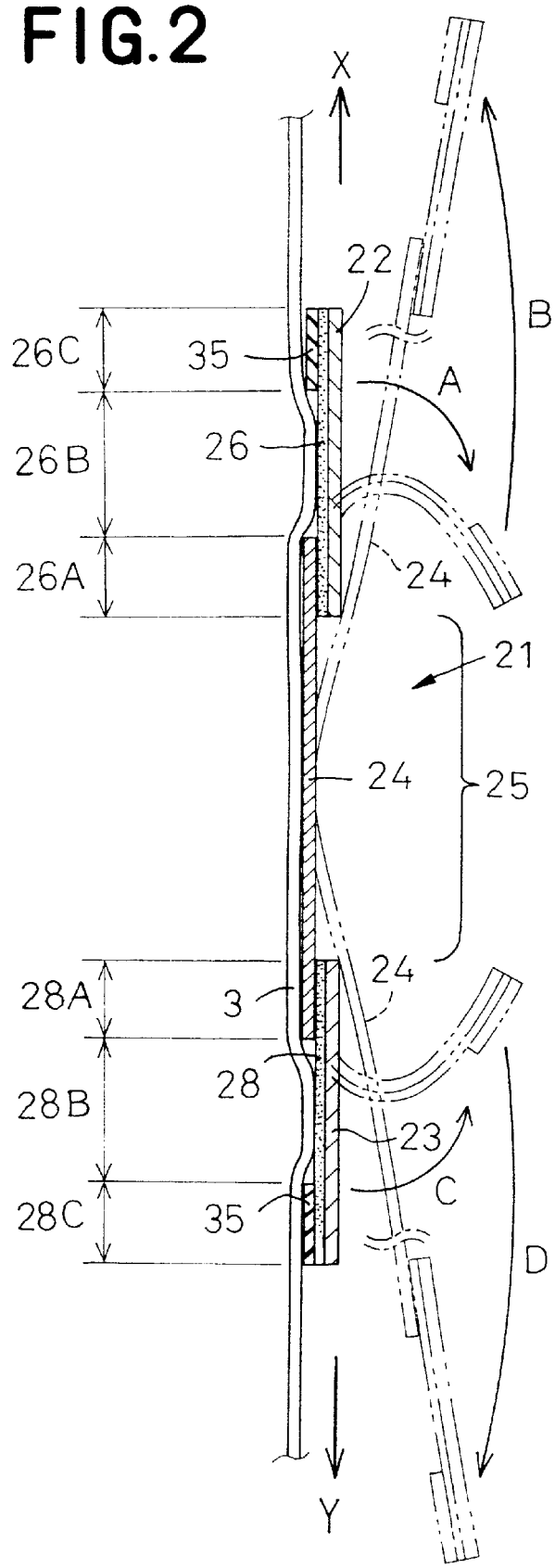
FIG. 2 is a sectional view taken along a line II—II in FIG. 1.

Details of a disposable body fluids absorbent garment with disposal securing means according to the invention will be more fully understood from the description of a disposable diaper as a specific embodiment of the invention given hereunder with reference to the accompanying drawings.

FIG. 1 shows a laminate structure 1 of a pull-on or pants type disposable diaper as viewed from a side of the wearer's back in a perspective view as partially broken away. The laminate structure 1 comprises a liquid-permeable topsheet 2, a liquid-impermeable backsheet 3 and a liquid-absorbent core 4 disposed between these two sheets 2, 3. The laminate structure 1 has a front waist region 6, a rear waist region 7 and a crotch region 8 extending between these two waist regions 6, 7. The front and rear waist regions 6, 7 are put flat and bonded together along their transversely opposite side edges 11, 12 so as to form a waist-opening 13 and a pair of leg-openings 14. The openings 13, 14 are provided along their peripheral edges with a plurality of elastic members 16 associated with said waist-opening 13 and a plurality of elastic members 17 associated with said leg-openings 14. The elastic members 16, 17 are bonded under their longitudinally stretched conditions, respectively, to an inner surface of a portion of the topsheet 2 and/or the backsheet 3 extending outward beyond a peripheral edge of the absorbent core 4. The rear waist region 7 is provided on an outer surface at its circumferentially middle with a tape fastener 21 adapted to be extendible upward as well as downward vertically of the diaper 1.

FIG. 2 is a sectional view taken along a line II—II in FIG. 1. As shown, the tape fastener 21 comprises, longitudinally (i.e., vertically as viewed in FIG. 2), an inelastic upper tape section 22, an inelastic lower tape section 23 and an elastic intermediate tape section 24 extending between the upper and lower tape sections 22, 23.

The upper tape section 22 has its entire inner surface applied with first adhesive 26. The area of the upper tape section 22 applied with the first adhesive 26 may be divided into vertically successive three sub-areas 26A, 26B, 26C. A first sub-area 26A is inseparably bonded to an upper end of the intermediate tape section 24 and a film strip 35 is bonded to a third sub-area 26C serving as an inadhesive hold on the upper tape section 22. A second sub-area 26B extending between the first and third sub-areas 26A, 26C is easily separated from the backsheet 3 under the effect of so-called peel force when the upper tape section 22 is folded back in a direction of an arrow A as indicated by imaginary lines. The second sub-area 26B is so arranged, on the other hand, that the second sub-area 26B is substantially inseparable from the backsheet 3 against so-called shear force acting between the upper tape section 22 and the backsheet 3 when the second sub-area 26B together with the backsheet 3 fastened to the second sub-area 26B is pulled in a direction of an arrow X.

The lower tape section 23 has substantially the same construction as that of the upper tape section 22. Specifically, the lower tape section 23 has its entire inner surface applied with second adhesive 28. The area of the inner surface applied with the second adhesive 28 is divided into vertically successive three sub-areas. A first sub-area 28A is inseparably bonded to a lower end of the intermediate tape section 24 and the film strip 35 is bonded to a third sub-area 28C. A second sub-area 28B extends between the first and third sub-areas 28A, 28C. The second sub-area 28B is easily separated from the backsheet 3 when the lower tape section 23 is folded back in a direction of an arrow C as indicated by imaginary lines. The second sub-area 28B is so arranged, on the other hand, that it is not easily separated from the backsheet 3 when the lower tape section 23 is pulled in a direction of an arrow Y.

The intermediate tape section 24 includes a sub-section 25 extending between the upper and lower tape sections 22, 23, which is extendible, more preferably, elastically stretchable vertically of the diaper laminate structure 1. Now it is assumed that the upper tape section 22 is folded off from the backsheet 3 in the direction of the arrow A as indicated by the imaginary lines with the lower tape section 23 remaining bonded to the backsheet 3, then unfolded in the direction of the arrow B and finally pulled in the direction of the arrow X (i.e., upwardly of the diaper 1). As a result, the intermediate tape section 24 is stretched as indicated by imaginary lines. It should be understood here that the lower tape section 23 is then substantially inseparable from the backsheet 3 as in the case when it is pulled in the direction of the arrow Y. Similarly, the intermediate tape section 24 is stretched downwardly of the diaper 1 when the lower tape section 23 is separated from the backsheet 3 in the direction of the arrow C with the upper tape section 22 remaining bonded to the backsheet 3, then unfolded in a direction of an arrow D and finally pulled in the direction of the arrow Y (i.e., downwardly of the diaper 1). It should be understood here that the upper tape section is then substantially inseparable from the backsheet 3 as in the case when it is pulled in the direction of the arrow X. In this manner, the tape fastener 21 is extendible, more preferably, elastically stretchable upward as well as downward vertically of the diaper 1 (see the imaginary lines in FIG. 1 also). The description "substantially inseparable" given above should be understood to mean that the respective tape sections 22, 23 are free from any apprehension that these tape sections 22, 23 which must remain fastened to the backsheet might be separated therefrom before the tape fastener 21 is extended to a length sufficient to roll up the diaper laminate structure 1 and consequently might make such extension of the tape fastener 21 impossible.

The upper and lower tape sections 22, 23 making part of the tape fastener 21 may be made of an inelastic polyester film or a nonwoven fabric. An example of such material is a polyester film having a thickness of 0.02~0.3 mm. The intermediate tape section 24 may be made of an extendible, more preferably, elastically stretchable plastic film, elastomer film, rubber sheet or the like. These materials also preferably have a thickness of 0.02~0.3 mm.

FIG. 3 is a perspective view showing the diaper 1 secured by the tape fastener 21 in its rolled up state. In the case of the example as shown, the used diaper 1 may be rolled starting from the crotch region 8 up toward the waist-opening 13, then the upper tape section 22 of the tape fastener 21 may be separated from the backsheet 3 and thereafter the tape fastener 21 may be stretched as shown by FIG. 2. Finally, the tape fastener 21 may be secured at its second sub-area 26B of the first adhesive 26 to the outer surface of the backsheet 3 on the far side of the waist-opening 13. It is also possible to follow the steps in the reverse order. Specifically, the used diaper 1 may be rolled starting from the waist opening 13 down toward the crotch region 8, then the lower tape section 23 may be separated from the backsheet 3 and thereafter stretched. Finally, the tape fastener 21 may be secured at its second sub-area 28B of the second adhesive 28 to the outer surface of the backsheet 3 on the far side of the crotch region 8.

Figure 4:
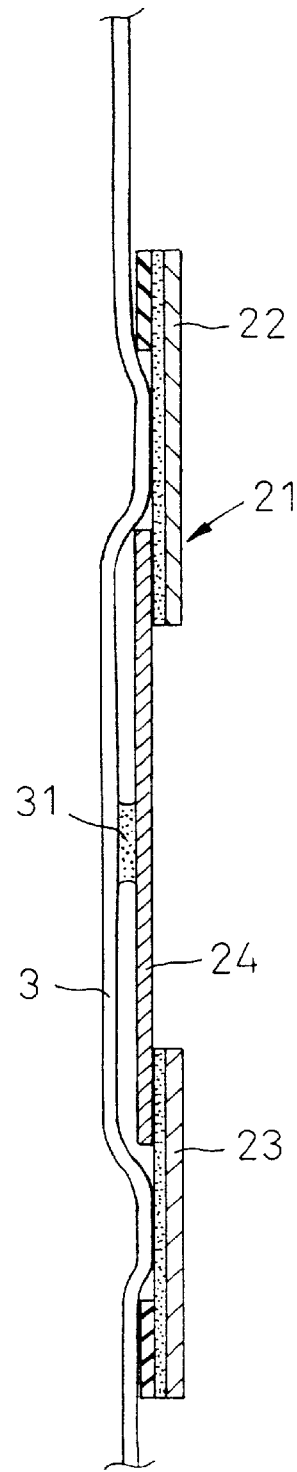
FIG. 4 is a view similar to FIG. 2 showing an alternative embodiment of the invention.

FIG. 4 is a view similar to FIG. 2 showing an alternative embodiment of the invention. According to this alternative embodiment also, the tape fastener 21 comprises the upper tape section 22, the lower tape section 23 and the intermediate tape section 24. In addition, in this fastener tape 21, the intermediate tape section 24 has its vertically middle sub-section firmly bonded to the outer surface of the backsheet 3 by means of adhesive 31 or heat-sealing. In this way, the tape fastener 21 is not easily separated from the backsheet 3 regardless of the directions in which the upper and lower tape sections 22, 23 are pulled.

According to the embodiments as have been described above, the first and second adhesive 26, 28 with which the upper and lower tape sections 22, 23 are applied may be well known pressure-sensitive adhesive usually applied on adhesive surfaces of tape fasteners attached to transversely opposite sides of a front or rear waist region and used to close a waist-loop of a so-called open type disposable diaper. In this regard, adhesive of different types can be selectively used for the first, second and third sub-areas 26A~26C, 28A~28C of the first and second adhesive 26, 28, respectively.

The term "inelastic" used in the description made above with respect to the upper and lower tape sections 22, 23 should be understood to mean that an amount by which these tape sections 22, 23 can be stretched is negligibly small compared to an amount by which the intermediate tape section 24 can be stretched during actual use of the tape fastener 21.

The disposable body fluids absorbent garment according to the invention is provided with the tape fastener used to roll up the used diaper for disposal and this tape fastener advantageously has the bidirectional extendibility. Accordingly, there is no apprehension that a wearer or a helper might roll up the used diaper in an improper direction.

What is claimed is:

1. A disposable body fluids absorbent garment comprising:

a laminate structure including a liquid-permeable topsheet, a liquid-impermeable backsheet and a liquid-absorbent core disposed between the liquid-impermeable topsheet and the liquid-impermeable backsheet; and a disposal securing means comprising a tape fastener having an extendible intermediate tape section and a pair of opposed inelastic ends, at least a portion of the extendible intermediate tape section being inseparably bonded to an outer surface of the liquid-impermeable backsheet and portions of the pair of opposed inelastic ends being temporarily fastened to the outer surface of the backsheet by means of an adhesive.

2. A disposable body fluids absorbent garment according to claim 1, wherein the pair of opposed inelastic ends are bonded to the extendable intermediate tape member.

3. A disposable body fluids absorbent garment according to claim 1, wherein the pair of opposed inelastic ends are provided with a non-adhesive film strip adjacent the portions thereof which are temporarily fastened to the outer surface of the backsheet.

4. A disposable body fluids absorbent garment according to claim 1, wherein the extendable intermediate tape section comprises an elastically extendable member.

5. A disposable body fluids absorbent garment according to claim 1, wherein the portion of the intermediate tape that is inseparably bonded to the outer surface of the liquid-impermeable backsheet comprises a middle portion thereof.

6. A disposable body fluids absorbent garment comprising a laminate structure formed by a liquid-permeable topsheet, a liquid-impermeable backsheet and a liquid-absorbent disposed between these two sheets; and a disposal securing means attached to an outer surface of said backsheet so as to be used to roll up said laminate structure, said disposal securing means comprises a tape fastener including an extendible intermediate tape section and a pair of inelastic and adhesive distal end tape sections extending from longitudinally opposite ends of said intermediate tape section in a direction in which said intermediate tape section is extendable wherein a region of said tape fastener extending between said pair of distal end tape sections and including said intermediate tape section is partially bonded to said outer surface of said backsheet so the said region is substantially inseparable from said outer surface of said backsheet when said tape fastener is pulled in an extension direction thereof, said tape fastener being temporarily fastened to said outer surface of said backsheet by means of adhesive at respective proximal ends of said distal end tape section, said proximal ends being contiguous to said intermediate tape sections, so that said proximal ends are easily separated from said outer surface of said backsheet when said distal end tape sections are pulled so as to be folded in a direction opposed to a direction in which they normally extend from said intermediate tape section, respectively, but said proximal ends are substantially inseparable from said outer surface of said backsheet when said distal end tape sections are pulled in said direction in which they normally extend from said intermediate tape section.

7. A disposable body fluids absorbent garment according to claim 6, wherein the intermediate tape section is partially bonded to said outer surface of said backsheet at a middle portion of the intermediate tape section.

\* \* \* \* \*